United States Patent
Baik et al.

(10) Patent No.: US 10,245,426 B2
(45) Date of Patent: Apr. 2, 2019

(54) MEDICAL PATCH

(71) Applicants: Industry-Academic Cooperation Foundation, Yonsei University, Seoul (KR); Seoul National University R&DB Foundation, Seoul (KR)

(72) Inventors: Hong Koo Baik, Seoul (KR); Woo Soon Jang, Seoul (KR); Tae Il Lee, Seoul (KR); Byung Soo Kim, Seoul (KR); Suk Ho Bhang, Seoul (KR); Wan Geun La, Cheonan-si (KR)

(73) Assignees: Seoul National University RDB Foundation, Seoul (KR); Industry-Academic Cooperation Foundation, Yonsei University, Seoul (KR)

( * ) Notice: Subject to any disclaimer, the term of this patent is extended or adjusted under 35 U.S.C. 154(b) by 348 days.

(21) Appl. No.: 14/261,534

(22) Filed: Apr. 25, 2014

(65) Prior Publication Data
US 2015/0182741 A1   Jul. 2, 2015

(30) Foreign Application Priority Data
Dec. 31, 2013   (KR) .......................... 10-2013-168808

(51) Int. Cl.
*A61N 1/36*    (2006.01)
*A61N 1/04*    (2006.01)
(Continued)

(52) U.S. Cl.
CPC ............ *A61N 1/0496* (2013.01); *A61L 15/26* (2013.01); *A61L 15/42* (2013.01); *A61N 1/0468* (2013.01);
(Continued)

(58) Field of Classification Search
CPC ............ A61B 8/0858; A61B 2562/028; A61B 2562/0285
See application file for complete search history.

(56) References Cited

U.S. PATENT DOCUMENTS 6,143,035 A  * 11/2000  McDowell ............. A61B 17/68
                                                    607/50
6,689,380 B1 *  2/2004  Marchitto ............. A61M 37/00
                                                    424/422
(Continued)

FOREIGN PATENT DOCUMENTS

JP          4437780           1/2010
JP        2012-141186         7/2012
(Continued)

OTHER PUBLICATIONS

Rusen Yang, Yong Qin, Cheng, Guang, and Zhong Lin Wang School of Materials Science and Eng, Georgia Institute of Technology, Atlanta, GA 30332 "Converting Biomechanical Energy into Electricity by a Muscle-Movement-Driven Nanogenerator" Nano Lett., 9 (3), pp. 1201-1205; DOI: 10.1021/nl803904b (Year: 2009).*
(Continued)

*Primary Examiner* — Michael D Abreu

(57) ABSTRACT

A medical patch having an electric potential generating structure which is attachable to a wound to thus regenerate injured skin tissues is provided. The medical patch includes a unit patch having a piezoelectric potential generating structure. The unit patch includes a first layer, a second layer and a piezoelectric nanomaterial disposed between the first and second layers.

21 Claims, 20 Drawing Sheets
(20 of 20 Drawing Sheet(s) Filed in Color)

Sc: subcutaneous tissue
Ep: epidermis
He: hypertrophic epidermis
De: dermis
Gr: granulation tissue
Pc: Panniculus carnosus
Mu: muscle
Arrowheads: arrows in Figures

(51) Int. Cl.
  *A61L 15/26* (2006.01)
  *A61L 15/42* (2006.01)
  *A61N 1/378* (2006.01)
  *B82Y 40/00* (2011.01)
  *B82Y 30/00* (2011.01)
  *H01L 41/113* (2006.01)

(52) U.S. Cl.
  CPC ......... *A61L 2400/12* (2013.01); *A61N 1/3785* (2013.01); *B82Y 30/00* (2013.01); *B82Y 40/00* (2013.01); *H01L 41/113* (2013.01)

(56) References Cited

U.S. PATENT DOCUMENTS

| | | | |
|---|---|---|---|
| 7,051,945 B2 | 5/2006 | Empedocles | |
| 8,588,930 B2* | 11/2013 | DiUbaldi | A61B 5/6874 607/71 |
| 2009/0171448 A1* | 7/2009 | Eli | A61B 17/22 623/1.32 |
| 2009/0226768 A1* | 9/2009 | Wang | H02N 2/18 429/2 |
| 2015/0336789 A1* | 11/2015 | Sodano | G01P 15/0922 257/415 |

FOREIGN PATENT DOCUMENTS

| | | |
|---|---|---|
| JP | 2013-26619 | 2/2013 |
| KR | 10-0807316 | 2/2008 |
| KR | 10-2009-0132416 | 12/2009 |
| KR | 10-2013-0024213 | 3/2013 |
| KR | 10-2013-0120848 | 11/2013 |
| WO | 2011/123560 | 10/2011 |
| WO | 2012/034110 | 3/2012 |

OTHER PUBLICATIONS

Woo Soon Jang et al., "Kinetically controlled way to create highly uniform mono-dispersed ZnO sub-microrods for electronics" Journal of Materials Chemistry, 22, p. 20719-20727 (Aug. 2012).

Tae Il Lee et al., "High-Power Density Piezoelectric Energy Harvesting Using Radially Strained Ultrathin Trigonal Tellurium Nanowire Assembly" Advanced Materials, 25, p. 2920-2925 (Apr. 2013).

\* cited by examiner

MEDICAL PATCH

CROSS REFERENCE TO RELATED APPLICATION

The present application claims priority from Korean Patent Application Number 10-2013-168808 filed on Dec. 31, 2013, the entire contents of which are incorporated herein for all purposes by this reference.

BACKGROUND OF THE INVENTION

Field of the Invention

The present invention relates to a medical patch, and more particularly, to a medical patch that can regenerate damaged skin tissues.

Description of Related Art

Various types of patches (also commonly referred to as bands) are used in order to treat wounds of the skin. These patches can be generally divided into two types. The first type is a patch that is attached to a wound of the skin in order to prevent secondary bacterial infection after a treatment ointment is applied on a portion of the skin that is wounded. When cells in the wound dry contact with the air, healing cells do not properly migrate around the wound, so that the expression of the cells is abnormal, thereby leaving a scar. In order to prevent this, a patch of the second type is made of a porous organic material having a large moisture content. When the second type of the patch is attached to the wound, moisture is discharged gradually from the porous organic material, thereby preventing necrosis of tissues.

Although these patches contain a treatment agent in order to heal the wound, a new type of a patch that treats a wound using an organic light-emitting diode (OLED) was introduced (e.g. Korean Patent Application Publication No. 10-2009-132416). However, this patch uses a large number of semiconductor devices, and requires other elements such as a positive pole, a negative pole, a battery and a microcontroller. In addition, this patch may cause several difficulties in everyday life, and therefore improvements are required.

The information disclosed in the Background of the Invention section is provided only for better understanding of the background of the invention, and should not be taken as an acknowledgment or any form of suggestion that this information forms a prior art that would already be known to a person skilled in the art.

BRIEF SUMMARY OF THE INVENTION

Various aspects of the present invention provide a medical patch having a novel structure that can regenerate wounded skin without containing a treatment agent.

Also provided is a medical patch having a novel structure that can regenerate wounded skin without a separate drive/control element such as a controller, just by attaching the medical patch to the skin.

Also provided is a medical patch having a novel structure that can regenerate wounded skin without causing difficulties in everyday life thanks to the simple structure.

In an aspect of the present invention, provided is a medical patch having an electric potential generating structure which is attachable to a wound to regenerate injured skin tissues. The medical patch includes a unit patch having a piezoelectric potential generating structure. The unit patch includes a first layer, a second layer, and a piezoelectric nanomaterial disposed between the first and second layers. The unit patch generates a piezoelectric potential by a muscle movement of the skin to which the patch is attached, without a separate electric potential generating system.

According to an embodiment of the present invention, the piezoelectric nanomaterial may include a plurality of piezoelectric nanorods.

The plurality of nanorods may be implemented as a plurality of biaxially-grown nanorods.

The plurality of nanorods may be arrayed unidirectionally between the first and second layers.

The plurality of nanorods may be arrayed unidirectionally to form a single layer between the first and second layers.

The first and second layers may be made of a material that is able to transfer mechanical energy applied from an outside to the piezoelectric nanorods.

The first and second layers may be made of a material that is able to transfer piezoelectric potential generated from the plurality of piezoelectric nanorods to a surface thereof.

The first and second layers may be flexible such that the patch is attachable to a skin for use.

The first and second layers may be made of a dielectric material having a dielectric constant. In this case, it is preferred that the first and second layers be made of polydimethylsiloxane (PDMS).

The unit patch may include a plurality of unit patches which are stacked one on another.

In another aspect of the present invention, provided is a medical patch having an electric potential generating structure which is attachable to a wound to regenerate injured skin tissues. The medical patch has a piezoelectric potential generating structure which includes a plurality of unit patches stacked one on another. Each of the plurality of unit patches includes a first layer, a second layer, and a plurality of piezoelectric nanorods disposed between the first and second layers. When the medial patch is attached to a skin for use, the piezoelectric potential generating structure converts mechanical energy originating from a movement of muscle into piezoelectric potential.

According to an embodiment of the present invention, each of the plurality of unit patches may share at least one of the first and second layers with an adjacent unit patch of the plurality of unit patches.

The number of the unit patches which are stacked one on another may vary depending on an intended level of potential.

The intended level of potential may be 1 V or higher.

The plurality of nanorods may be arrayed unidirectionally between the first and second layers.

The plurality of nanorods may be arrayed unidirectionally to form a single layer between the first and second layers.

The plurality of nanorods may be implemented as a plurality of biaxially-grown nanorods.

The first and second layers may be made of a material that is able to transfer mechanical energy applied from an outside to the layer of piezoelectric nanorod members.

The first and second layers may be made of a material that is able to transfer piezoelectric potential generated from the plurality of piezoelectric nanorods to a surface thereof.

The first and second layers may be flexible such that the patch is attachable to the skin for use.

The first and second layers may be made of a dielectric material having a dielectric constant. In this case, it is preferred that the first and second layers be made of PDMS.

In a further aspect of the present invention, provided is a method of fabricating a medical patch having an electric potential generating structure which is attachable to a wound to regenerate injured skin tissues. The method includes the following steps of: (a) preparing powders of piezoelectric nanorods; (b) forming a layer of piezoelectric nanorods by dispersing and rubbing the powders of piezoelectric nanorods on a first layer which is coated on a substrate; (c) forming a second layer on the layer of piezoelectric nanorods; and (d) forming a unit patch having a piezoelectric potential generating structure by separating the first layer and the substrate from each other.

The plurality of piezoelectric nanorods may be implemented as a plurality of biaxially-grown nanorods.

The step (b) may include arraying the plurality of nanorods unidirectionally between the first and second layers.

The step (b) may include arraying the plurality of nanorods unidirectionally to form a single layer between the first and second layers.

The first and second layers may be made of a material that is able to transfer mechanical energy applied from an outside to the layer of piezoelectric nanorod members.

The first and second layers may be made of a material that is able to transfer piezoelectric potential generated from the plurality of piezoelectric nanorods to a surface thereof.

The first and second layers may be flexible such that the patch is attachable to a skin for use.

The first and second layers may be made of a dielectric material having a dielectric constant, and preferably, PDMS.

The method may further include the step of stacking a plurality of the unit patches one on another.

The plurality of biaxially-grown piezoelectric nanorods may be fabricated by hydrothermal synthesis.

As set forth above, the medical patch is configured such that it can generate electric potential without a separate power source unlike conventional medical bands or patches. When a patch is configured such that a piezoelectric nanomaterial (e.g. piezoelectric nanorods) is disposed between specific thin films, electric potential is generated from the piezoelectric nanorods in response to the muscle movements of the skin to which the patch is applied. The electric potential can achieve the skin regeneration effect by stimulating the skin. Accordingly, it is possible to provide the medial patch that can regenerate the skin without having to employ a complicated structure or complicated elements, such as a semiconductor device or battery, or without using a treatment ointment.

The methods and apparatuses of the present invention have other features and advantages which will be apparent from, or are set forth in greater detail in the accompanying drawings, which are incorporated herein, and in the following Detailed Description of the Invention, which together serve to explain certain principles of the present invention.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Reference will now be made in detail to exemplary embodiments of the present invention in conjunction with the accompanying drawings. Herein, detailed descriptions of functions and components well known in the art will be omitted. For instance, detailed descriptions of a method of synthesizing/fabricating uniaxial nanorods and biaxially grown nanorods and a process of aligning nanorods through rubbing will be omitted since such method and process are well known in the art involving the arrangement of liquid crystal. Even if such descriptions are omitted, the constructions, functions and so on of a medical patch according to the present invention will be apparent to a person skilled in the art from the following description.

The configuration of the patch according to an embodiment of the present invention is completely different from those of conventional patches. That is, the patch is attached to the skin, and muscles of the skin to which the patch is attached move normally. The inventors have made the present invention by devising a structure capable of generating piezoelectric potential in order to convert the mechanical movements of the muscles into electric potential, and applying this structure to a medical patch. The medical patch was attached to the skin in order to check whether or not a wound was regenerated.

Reference will now be made in detail to a medical patch according to the present invention, exemplary embodiments of which are illustrated in the accompanying drawings and described below.

Figure 1:
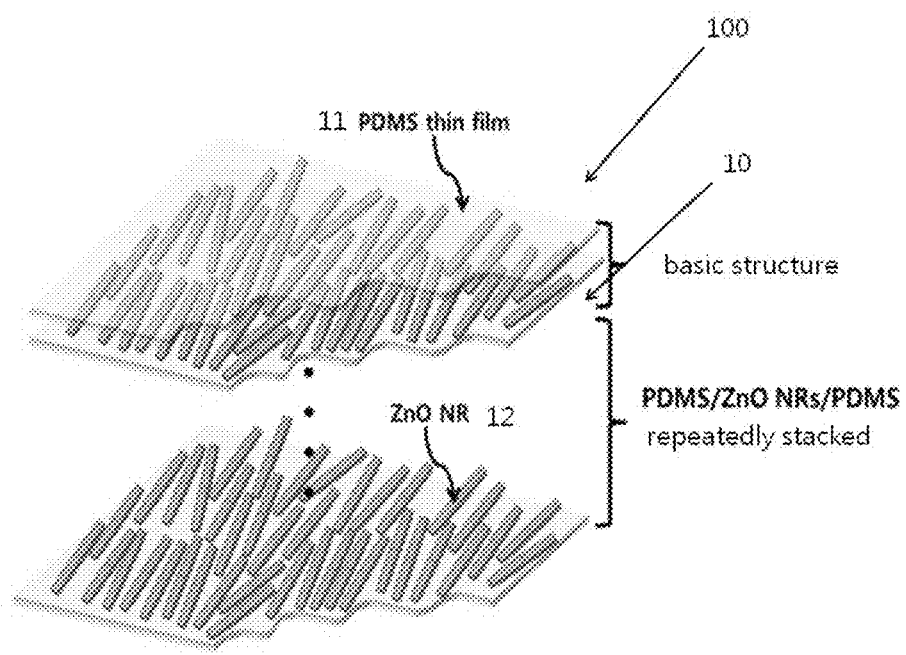
FIG. 1 is a conceptual view showing a schematic structure of a medical patch according to one embodiment of the present invention.

FIG. 1 is a conceptual view showing a schematic structure of a medial patch 100 according to one embodiment of the present invention.

As shown in the figure, the medical patch 100 includes a plurality of polydimethylsiloxane (PDMS) thin films 11 and a plurality of layers of nanorods 12. The layers of nanorods 12 are respectively disposed between the PDMS thin films 11, thereby forming a plurality of unit patches 10 which are stacked one on another. In the plurality of unit patches 10, each unit patch 10 may share at least one of the first and second PDMS thin films 11 with the adjacent unit patch 10. The nanorods according to this embodiment are implemented as, but not limited to, Zinc oxide (ZnO) nanorods. ZnO is merely an example of typical piezoelectric materials, and any piezoelectric material that can convert external mechanical force into electric potential is applicable to the present invention. For instance, a variety of other piezoelectric materials, such as ZnO, $ZnSnO_3$, GaN, Te, CdTe, CdSe, $KNbO_3$, $NaNbO_3$, InN, PVDF and PVDF-TrFE, can be used. The term "nanorods" used in the specification and the appended Claims is commonly used by those skilled in the art to which the present invention relates, and the aspect ratio of nanorods is typically 10 or less. In many cases, the size of "nano" is referred to as being 100 nm or less in the art. It should be understood that the term "nanorods" is interpreted as a material, the technical meaning of which is consistent with its meaning in the context of the relevant art. ZnO nanorods used in this embodiment has a length ranging approximately from 2.5 to 3 μm and a diameter ranging approximately from 200 to 250 nm. A one-dimensional nanomaterial of such a small size has a characteristic in that a lattice strain can be easily induced by a small amount of external mechanical energy (bending or shaking).

The PDMS thin films 11 form the exterior structure of the medial patch, and serve to firmly support the nanorods made of a piezoelectric material disposed between the two PDMS thin films. The PDMS is a dielectric material having a dielectric constant, and is flexible such that it can be attached to any region of the skin. However, the present invention is not limited to such PDMS materials, but any dielectric material having flexibility and a dielectric constant can be applied to the present invention. Specifically, the present invention can employ any dielectric material that has a dielectric constant and can transfer piezoelectric potential generated from a piezoelectric material. It is more preferable that the dielectric material is flexible so as to be attached to any object and can transfer external mechanical energy to the piezoelectric material without a significant loss. In consideration of such conditions, the PDMS is used in exemplary embodiments of the present invention.

Figure 3:
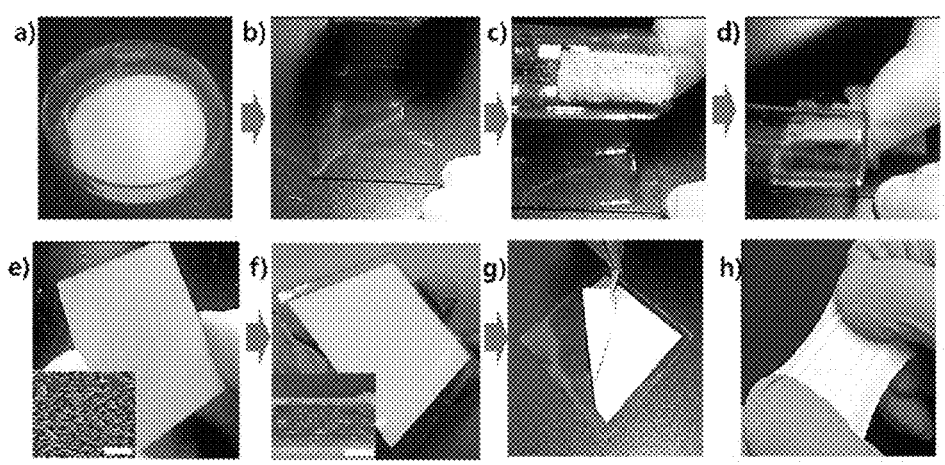
FIG. 3 is a view showing the process of fabricating a unit patch having a piezoelectric potential generating structure according to an embodiment of the present invention.

A description will be given below to the process of manufacturing the unit patch 10 with reference to FIG. 3. FIG. 3 schematically shows an example in which the unit patch 10 is manufactured according to one embodiment of the present invention.

Figure 2:
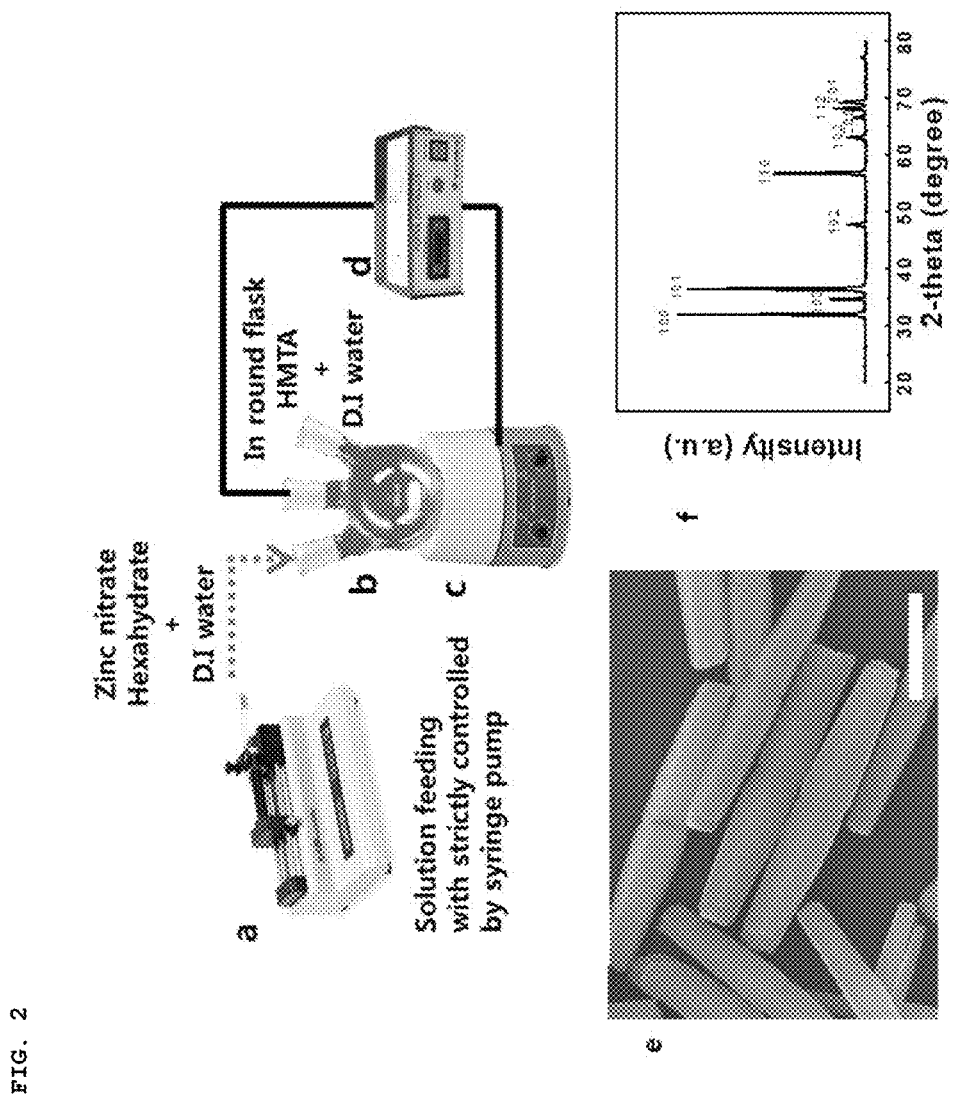
FIG. 2 is a view showing a system for synthesizing biaxially grown ZnO nanorods according to an exemplary embodiment of the present invention.

According to an exemplary embodiment of the present invention, biaxially-grown ZnO nanorod powders were prepared through hydrothermal synthesis (Woo Soon Jang et. al, Kinetically controlled way to create highly uniform mono-dispersed ZnO sub-microrods for electronics, *J. Mater. Chem.*, 22, 20719-20727 (2012); The disclosure of which is incorporated herein in its entirety.) A system for synthesizing biaxially-grown ZnO nanorods, a scanning electron microscopy (SEM) image and an X-ray diffraction (XRD) spectrum are schematically shown in FIG. 2. Describing in detail, in this synthesis process, the inventors continuously added a Zn precursor solution into a hot solution of hexamethylenetetramine (HMTA, $C_6H_{12}N_4$, 99+%, available from Aldrich) using a syringe pump. According to typical synthesis, two precursor solutions were prepared by separately dissolving 0.42 g zinc nitrate hexahydrate ($Zn(NO_3)_2 \cdot 6H_2O$, ≥99.0%, available from Aldrich) into 100 mL deionized water (at room temperature) and 0.24 g HMTA into 100 mL deionized water (at room temperature). The Zn precursor solution was injected continuously into the HMTA solution at a rate of 2 mL/h for 25 minutes using the syringe pump, and the process was completed after 5 minutes. After centrifugation, flocculated nanorods were isolated from supernatant, and washed three times with deionized water to remove unreacted $Zn^{2+}$ and other ions. Final precipitate was dried at 80° C. and thermally annealed at 400° C. for 2 hours in a vacuum to improve crystallinity. Finally, biaxially-grown ZnO nanorod powders were synthesized, as shown in part a) of FIG. 3. The piezoelectric mechanism in which the biaxially-grown ZnO nanorods employed in this embodiment generate electric potential will be discussed separately below.

Afterwards, a slide glass was coated with a first PDMS film (with a thickness of about 1.5 μm), as shown in part b) of FIG. 3. The above-synthesized ZnO nanorods were disposed on the coated PDMS film, and a unidirectional single layer of ZnO nanorods was formed using a piece of velvet cloth and through rubbing, as shown in parts c) and d) of FIG. 3. Part e) of FIG. 3 shows the unidirectional single layer of ZnO nanorods formed on the PDMS film. The nanorods were formed unidirectionally according to this embodiment in consideration of the direction in which the patch is bent when the patch is applied to the skin. Specifically, the muscles of the skin having the patch attached thereto will move in random directions or a plurality of directions. However, in some cases, the muscles may move in one direction. In consideration of this and in order to maximize the generation of electric potential, the nanorods are arrayed unidirectionally. However, the nanorods are not necessarily formed unidirectionally, but can be formed in random directions. The nanorods can be arrayed so as to form not only a single layer but also multi layers. (The single layer of nanorods is preferable since the nanorods may interfere with each other to damage each other while being bent when the multi layers of nanorods are formed.) The present invention does not specifically limit the array of the nanorods which are made of a piezoelectric material and disposed between the PDMS films. However, according to this exemplary embodiment, the nanorods are arrayed to form a unidirectional single layer in order to maximize the generation of piezoelectric potential using small mechanical motion.

In subsequence, the unidirectional single layer of ZnO nanorods on the first PDMS film is coated with a second PDMS film, as shown in part f) of FIG. 3. Afterwards, the PDMS films are separated from the slide glass, as shown in part g) of FIG. 3, thereby fabricating a unit patch 10 having a piezoelectric structure (including the first PDMS film, the unidirectional single layer of ZnO nanorods and the second PDMS film), as shown in part h) of FIG. 3.

Afterwards, a unidirectional single layer of ZnO nanorods was formed again on the unit patch 10 through the processes shown in the parts (c) and (d) of FIG. 3. These processes are repeated several times, thereby manufacturing a medial patch 100 in which a plurality of unit patches 10 are stacked one on another. The present invention is not limited to the medial patch 100 in which the unit patches 10 are stacked one on another. It is possible to manufacture the medial patch 100 by stacking a plurality of unit patches 10 one on another so as to generate electric potential as intended or use the unit patch 10 itself as a medical patch, and both of such examples fall within the scope of the present invention.

Figure 4:
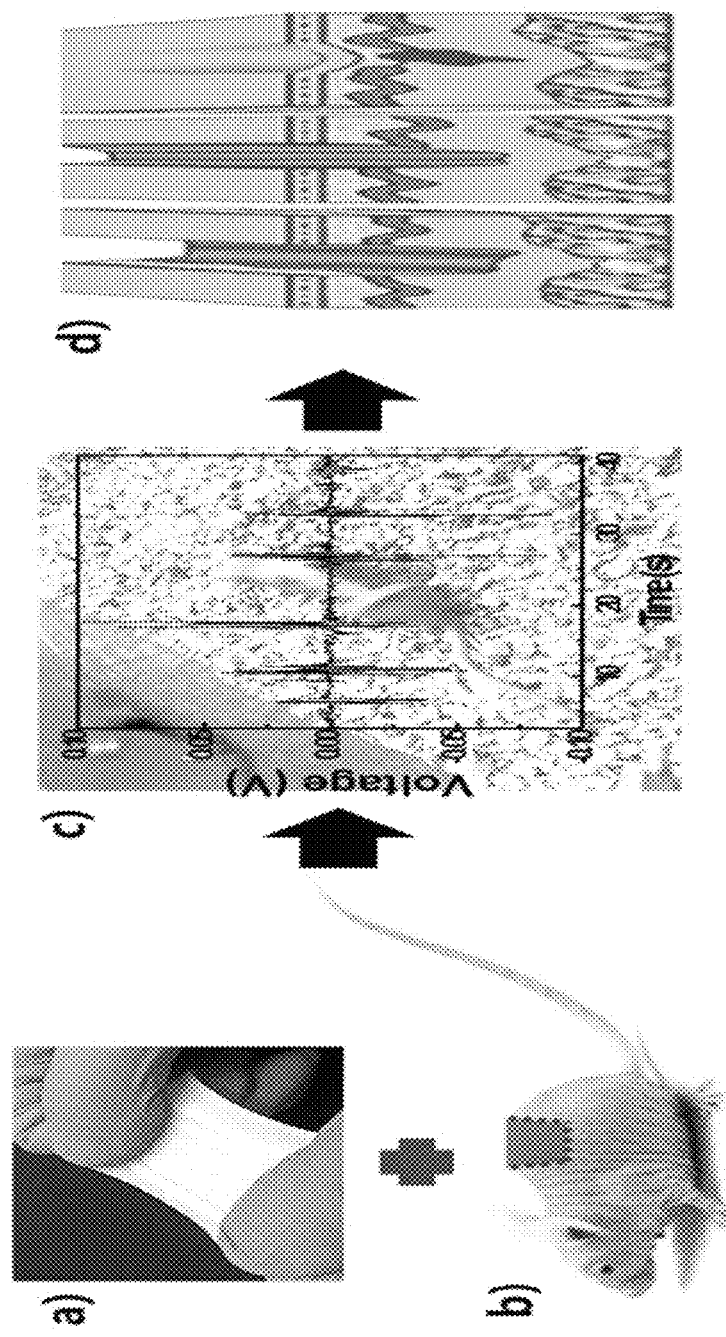
FIG. 4 is a schematic view showing the progress of a process in which a medical patch according to an embodiment of the present invention is applied to an animal test.

In order to see whether or not the medial patch 100 configured as above is medically applicable, the inventors tested the medial patch 100 on animals prior to clinical trials. Specifically, as shown in FIG. 4 which schematically illustrates the experimental procedures of this example, a part of the back of each nude mouse was dissected, and the medial patch 100 which was prepared as described above was attached to the dissected part. The patch was fixed to the wound using a Tegaderm film (available from 3M, MO, USA) (which is generally used as a wound dressing), as shown in part b) of FIG. 4. The medial patch 100 used in this example was composed of 9 unidirectional single layers of ZnO nanorods such that electric potential of at least 1V was generated in order to facilitate the regeneration of the skin. Afterwards, nude mice were moved into cages, and the regeneration of the skin and the skin tissues was analyzed for a predetermined period, as shown in parts c) and d) of FIG. 4.

In this test, mouse skin wound closing models were prepared by dissecting the skin of the back of each mouse in a size of 2 cm×2 cm. A total of 5 test groups were prepared, including 1) negative control group (no treatment), 2) fibrin gel application group (positive control group; Biodegradable and biocompatible hydrogel was used for skin wound closing treatment), 3) test group to which only the PDMS was attached, 4) PZ-0.5 test group in which piezoelectric potential intensity was halved (The thickness of the PDMS was doubled or the amount of ZnO nanorods was halved compared to PZ test group), and 5) PZ test group in which piezoelectric potential intensity was maintained. The test was conducted for a total of 2 weeks. The levels of skin regeneration in the wounds were monitored and compared, and the results are presented in FIG. 5.

Figure 5:
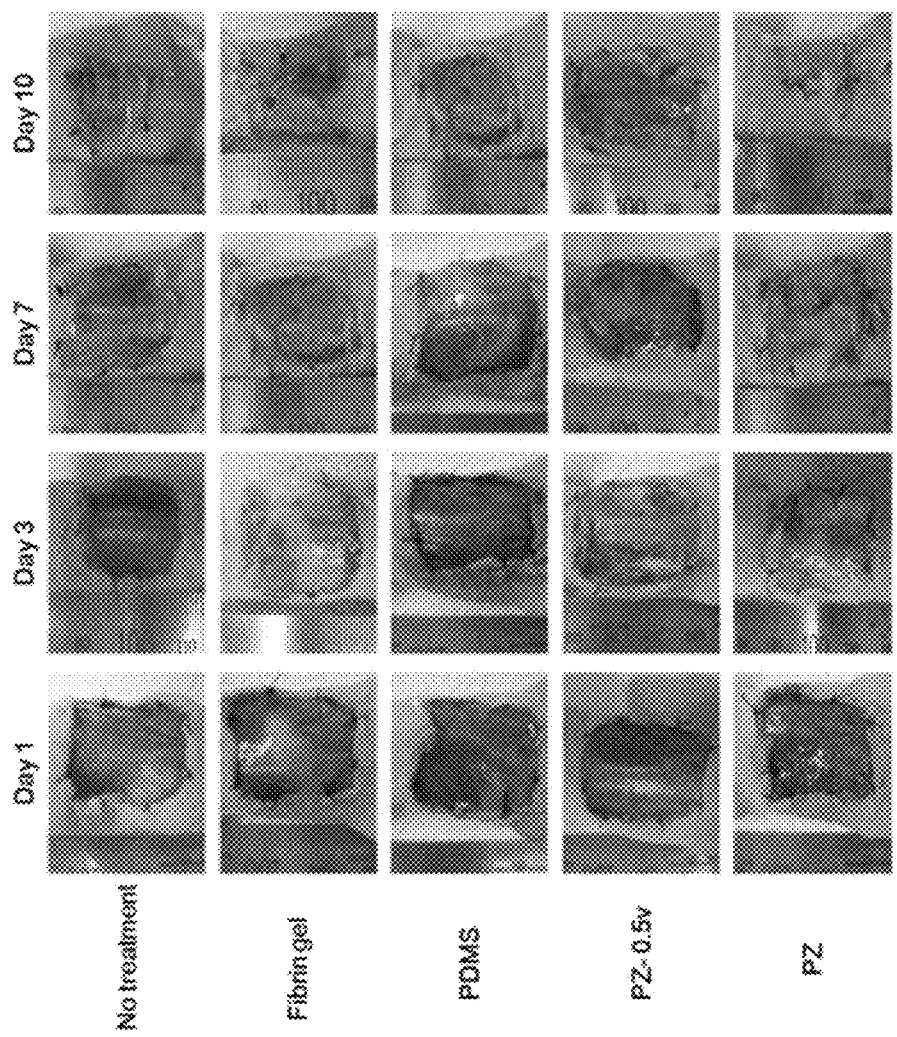
FIG. 5 is pictures showing wound treatment processes over time in five test groups used in the animal test according to one embodiment of the present invention.
Figure 6:
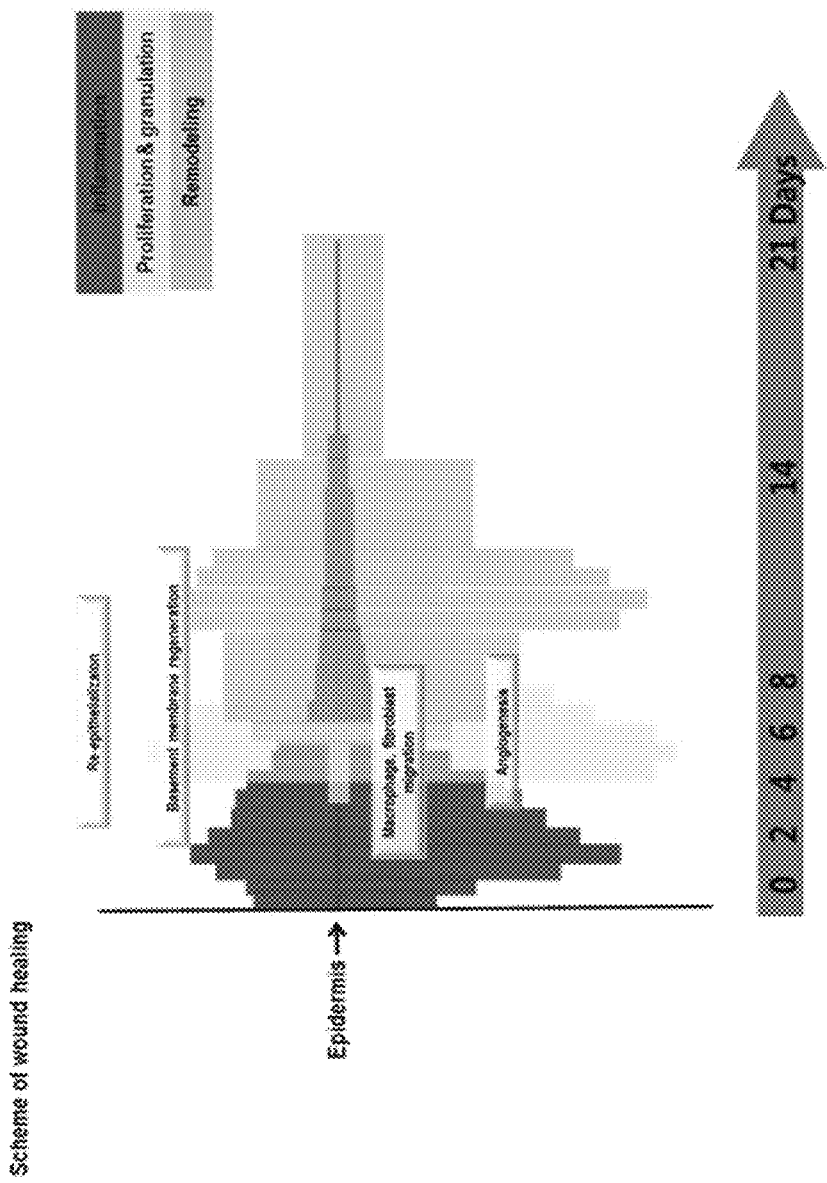
FIG. 6 is a view showing a skin regeneration mechanism over time.

FIG. 5 shows the entire process of wound regeneration over time after the mouse skin wound closing models were prepared. In the PZ test group in which piezoelectric potential intensity was maintained (the test group in which the medical patch 100 was applied), the appearance of rapid skin regeneration was identified. Such changes in the appearance were caused by the skin regeneration mechanism over time shown in FIG. 6, and are divided into an inflammatory reaction period, a cell proliferation period and a tissue regeneration period. Changes in the overall appearance were quantitatively identified by the period. When the piezoelectric potential generating material was used, rapid skin would closing was identified up to 10 days. This result was proved to be superior to that of conventional fibrin gel, i.e. the medical ointment used for the regeneration of the skin. The PZ-0.5 test group (the test group in which piezoelectric potential intensity was halved) also showed the effect of skin regeneration, which, however, was lower than that of the PZ test group. In conclusion, the medial patch 100 according to the present invention can help the skin regenerate.

Figure 7:
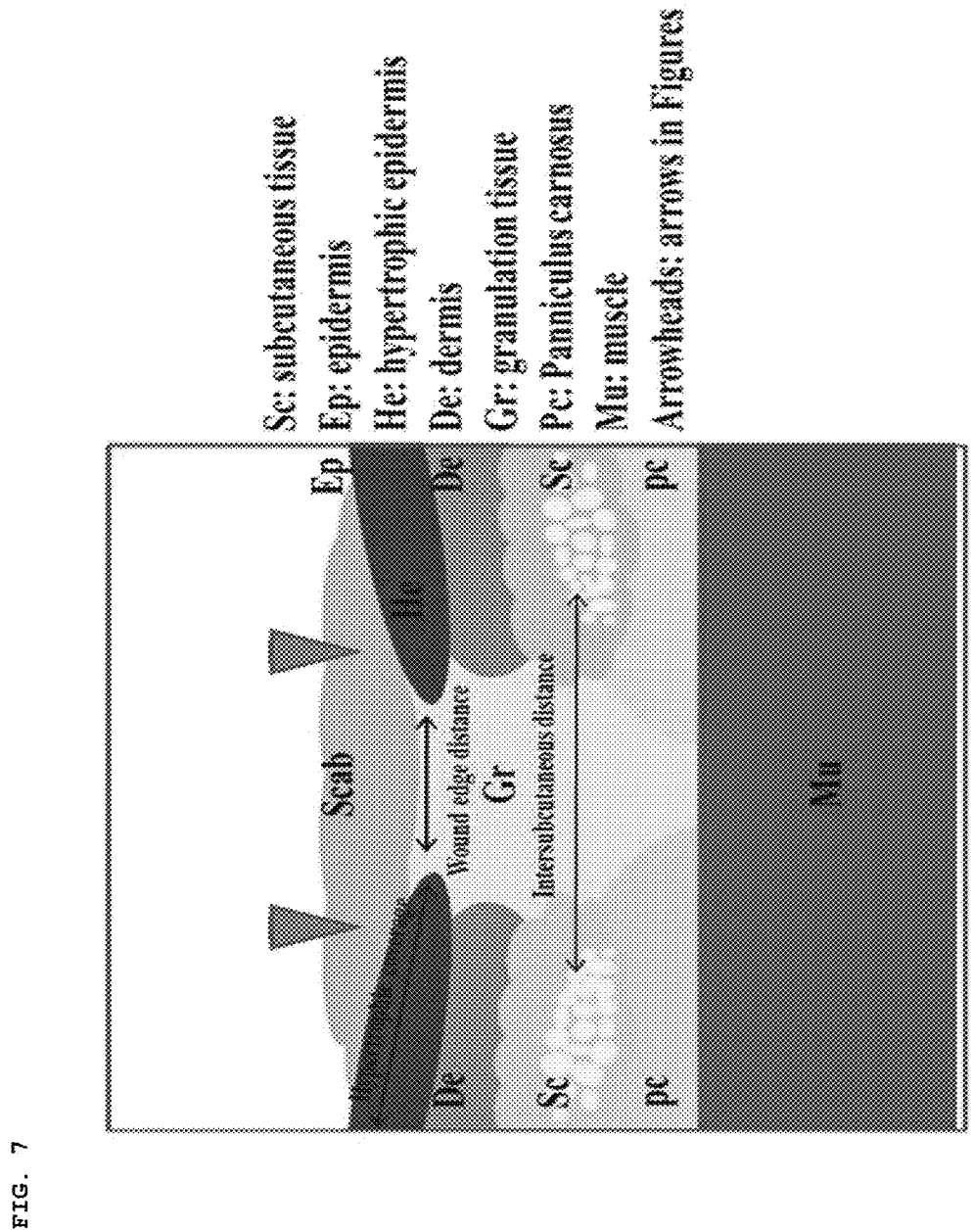
FIG. 7 is a view showing the skin structure of a wound.
Figure 8:
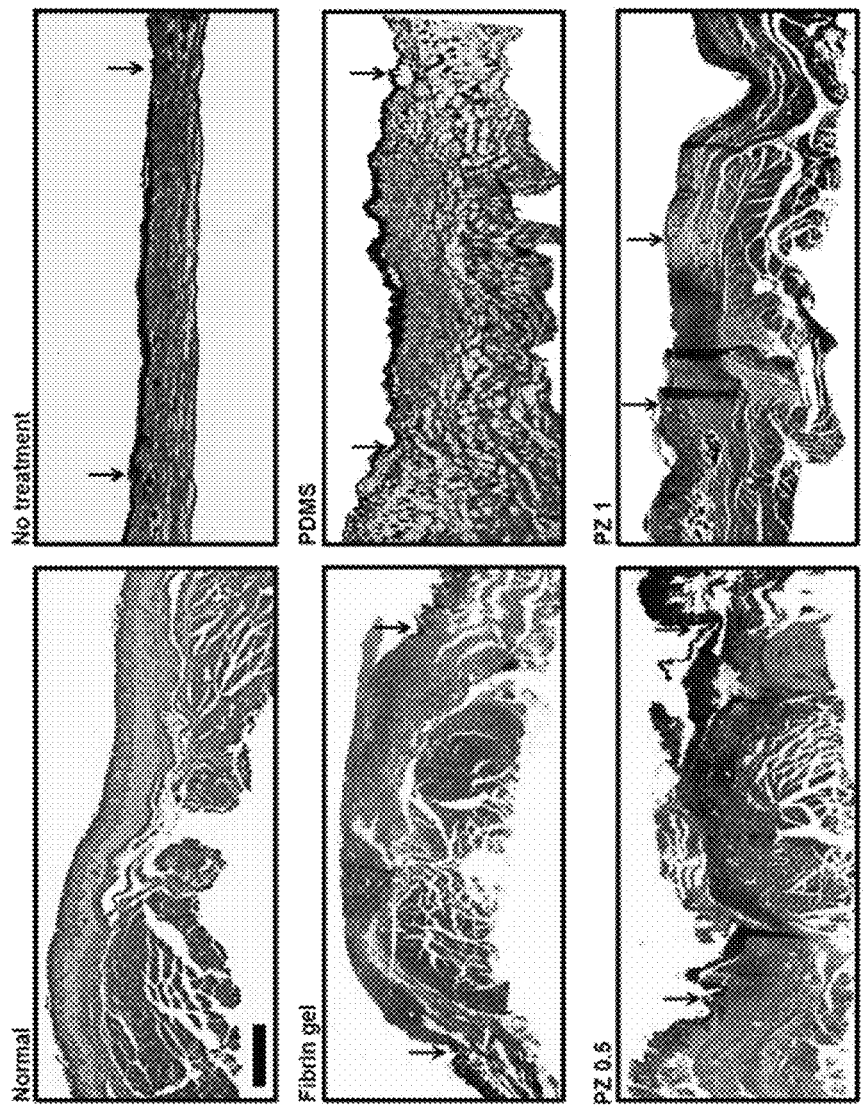
FIG. 8 is a view showing the muscle tissues of a normal group and the five test groups.

In order to identify differences between the tissue regeneration phases, the skin tissues of the wounds were compared after 14 days. In order to compare the overall levels of skin regeneration, stained histological analysis, more particularly, hematoxylin and eosin staining (H&E) was conducted, as shown in FIG. 8. A structure of tissue layers specific to the skin, including an epidermal layer, a dermal layer, a layer of fat and a layer of muscles, clearly appeared in the normal group, as shown in FIG. 7 and the upper left image of FIG. 8. However, in the other test groups except for the PZ test group to which the medial patch 100 according to this embodiment was applied, no clear structures of tissue layers were identified, but fibrosis caused by tissue necrosis or a mixture of several tissue layers was identified. As for the PZ-0.5 test group and the test group in which the fibrin gel was used, an improvement in the boundary of the muscle layer was identified compared to the negative control group or the test group to which only the PDMS was attached. However, the boundary between the dermal layer and the epidermal layer was insignificant and some of the tissue layers were mixed. It was thus identified that the skin tissues were not regenerated normally. (The PZ-0.5 test group was proved to be able to regenerate the skin to a certain level, although the tissue layer structure of the PZ-0.5 test group was not clear compared to the PZ test group.)

Figure 9:
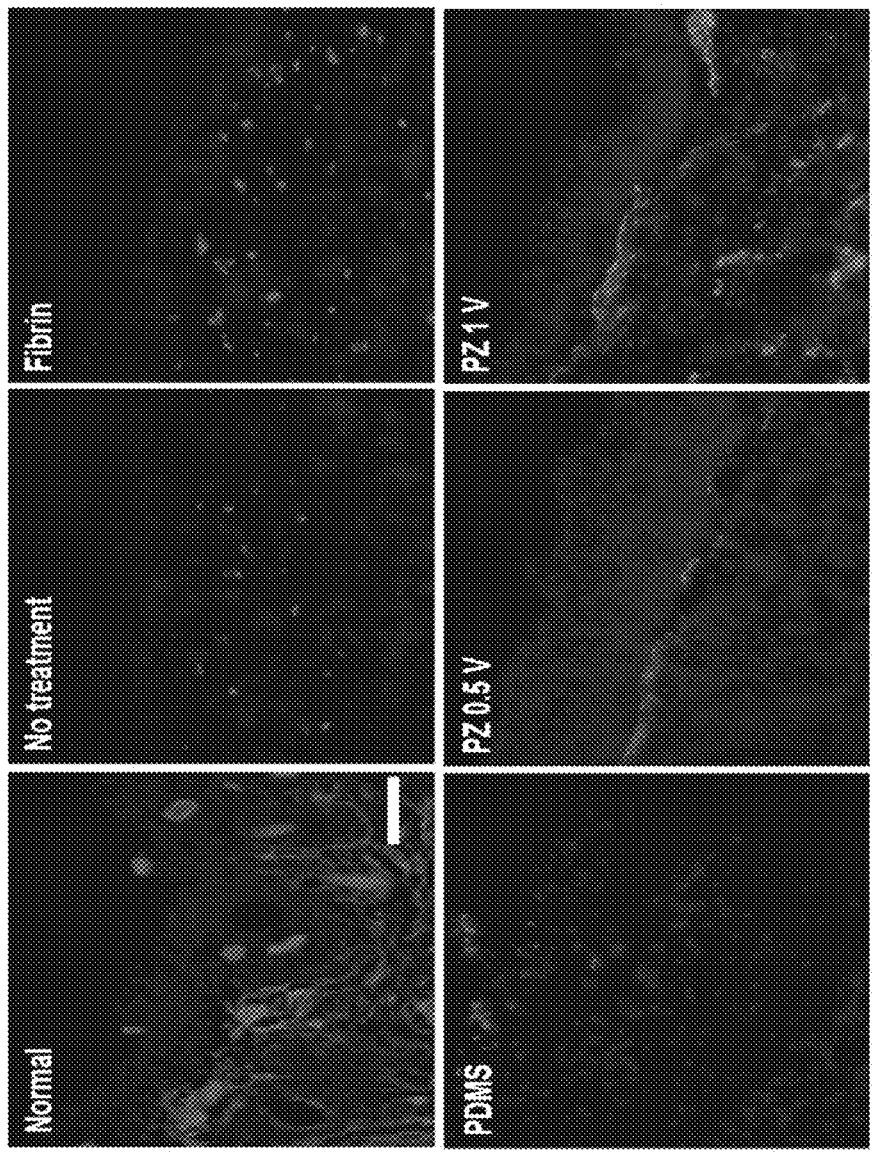
FIG. 9 is a view showing the presence and distribution of laminin protein in the normal group and the five test groups obtained through fluorescent immunostaining.
Figure 10:
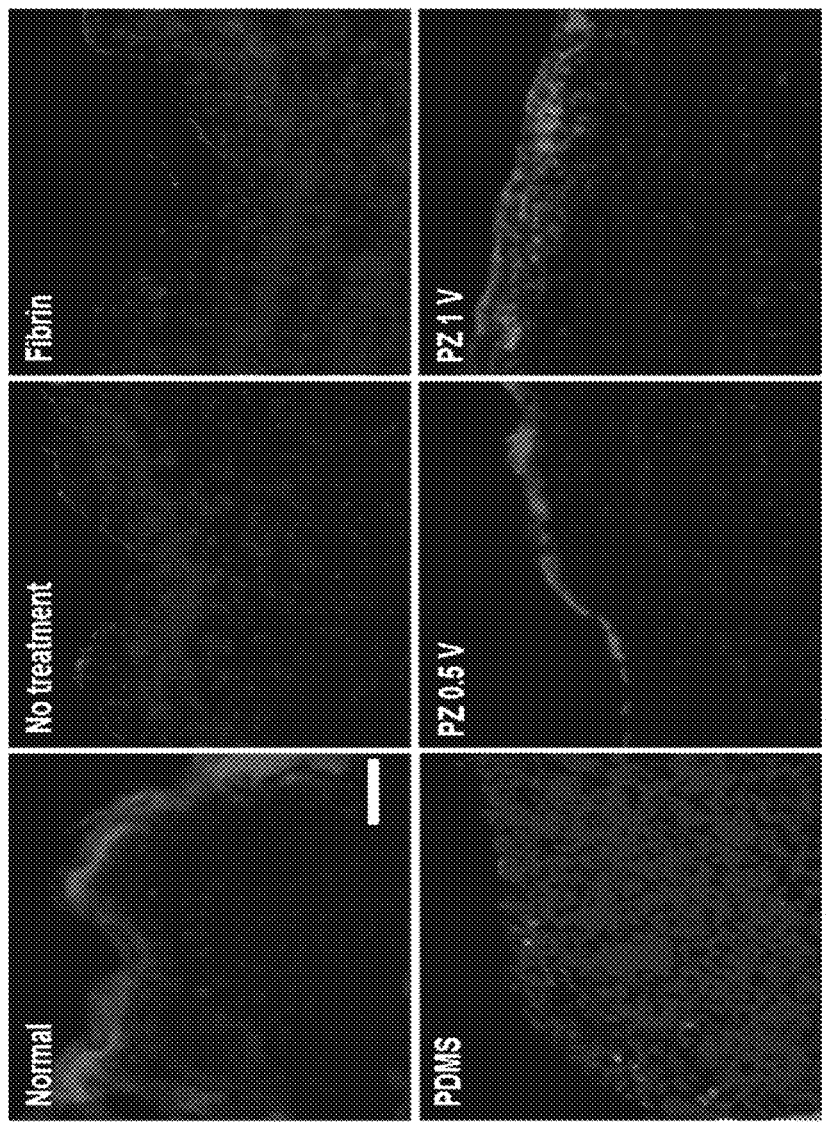
FIG. 10 is a view showing the presence and distribution of involucrin protein in the normal group and the five test groups obtained through fluorescent immunostaining.

In order to identify the completeness of the regenerated skin tissues compared to a normal skin tissue, the presence and distribution of laminin protein (red regions in FIG. 9) and involucrin protein (red regions in FIG. 10) which exist in regenerated tissues were observed through fluorescent immunostaining. The laminin protein were identified as being uniformly distributed in the normal tissue. In contrast, only partial distribution of the laminin and involucrin protein was observed in the negative control group, the fibrin gel application test group and the PZ-0.5 test group. The observed quantitative distribution was also significantly smaller than that of the PZ test group. (The distribution of the laminin and involucrin proteins observed in the PZ-0.5 test group was wider than those of the other test groups.) The results exhibit that the effect of skin regeneration in the dermal and epidermal layers of the skin with the use of the medial patch 100 according to this embodiment is superior to those of the other test groups. The wound or skin can be regenerated to a level similar to that of the normal tissue.

The degrees of progress of the skin regeneration mechanism over time were identified by western blot analysis. As a result, at the initial inflammatory reaction period (day 3), the development of inflammatory reaction factors, such as keratin 14 or CD68, in the PZ test group was considerably high compared to those in the other test groups. This phenomenon indicates that the electric potential (the electrical signal) from the medial patch 100 acts effectively in order to prevent the necrosis of the tissue and introduce cells necessary for regeneration from normal tissues of the host at an early stage of the skin regeneration. At day 10, factors related to cell proliferation were checked, and the development of growth factor (TGF-$\beta$), reproduction factor (MMP-2) for the preparation of tissue regeneration, or the like was increased most in the PZ test group. This explains that a sufficient amount of cells and tissues for wound regeneration migrated into the wound over the inflammatory reaction period and the tissue regeneration period was thus activated. Although not shown in the figures, the amounts of the expression of fibronectin and collagen type IV that show the completeness of the regeneration of skin tissue were checked in order to compare the levels of tissue regeneration. The expression was significantly increased in the PZ test group unlike the other groups including the negative control group.

The results explain that the expression of the factors for skin wound regeneration and the levels of tissue regeneration based on those factors were accelerated when the medial patch 100 having the piezoelectric potential generating structure according to this embodiment was used. The amounts of expression of laminin and involucrin which were checked in FIG. 9 and FIG. 10 were quantitatively checked again by western blot analysis at day 14 (not shown). When checked from the cross-section of the regenerated skin, it was identified again that the amount of each protein increased over the entire area of skin regeneration in the PZ test group.

In order to complete the normal regeneration of the skin, new blood vessels must be formed in the area of regeneration so that blood can be properly supplied to the regenerated area during the regeneration or after the completion of the regeneration. Therefore, in order to identify vessels having a small diameter formed in the regeneration area, CD31

Figure 11:
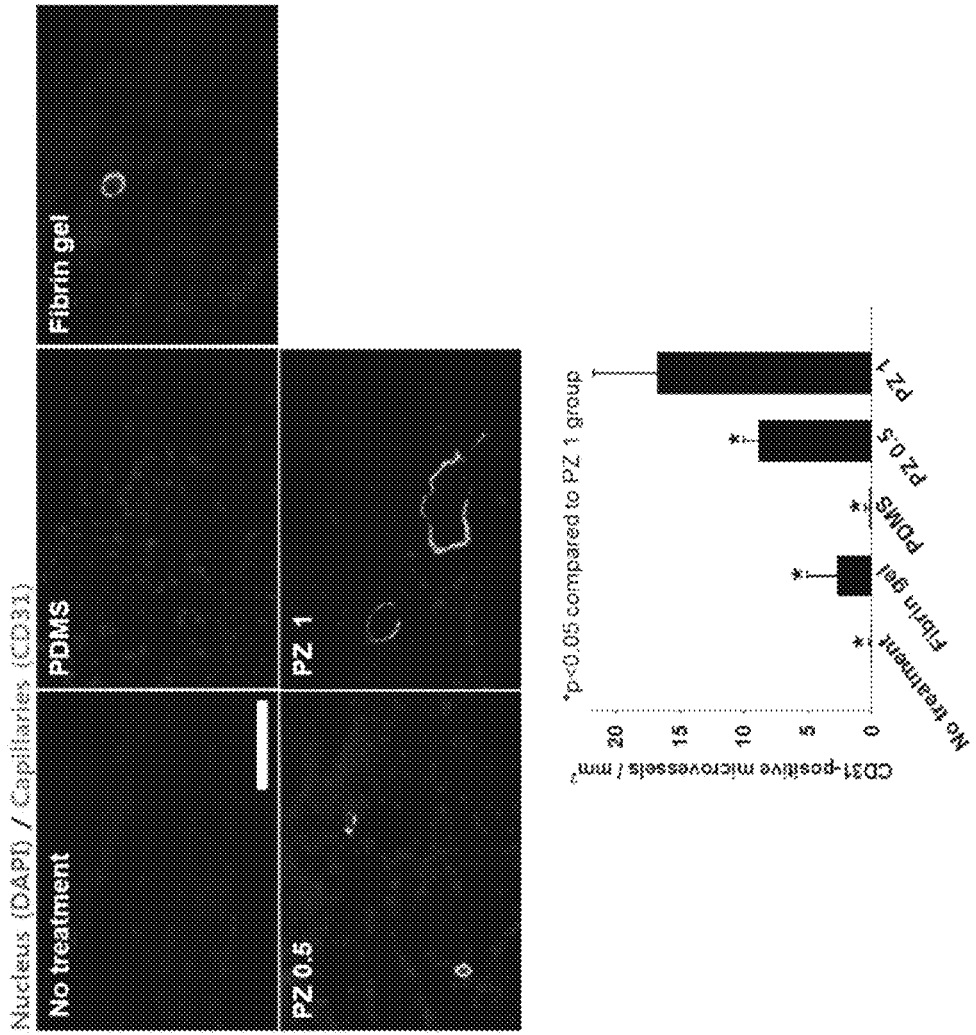
FIG. 11 is a view showing the formation of capillaries in the regenerated skin obtained through CD31 fluorescent immunostaining.
Figure 12:
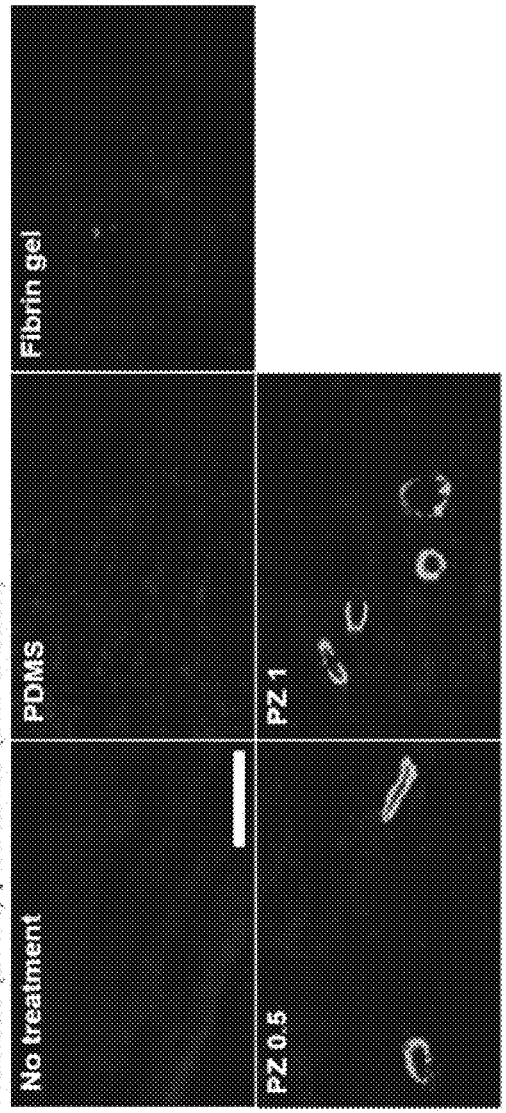
FIG. 12 is a view showing the formation of arteries in the regenerated skin obtained through SM-α actin fluorescent immunostaining.
Figure 12:
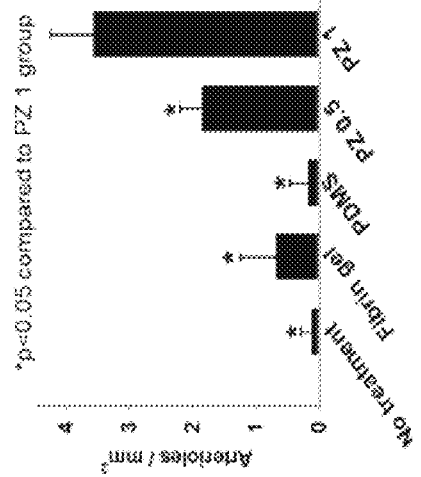

(capillaries, FIG. 11) and SM-α actin (arterioles, FIG. 12) fluorescent immunostaining was performed, and the results of the groups were compared. As a result, the formation of capillaries and arterioles in the regeneration area was identified as being significantly increased in the PZ test group compared to the other groups. This explains that the use of the medial patch 100 having the piezoelectric potential generation structure can continue and maintain the treatment of the wound through the increased new blood vessels.

Piezoelectric Behaviors of Biaxially-Grown ZnO Nanorods

Figure 13A:
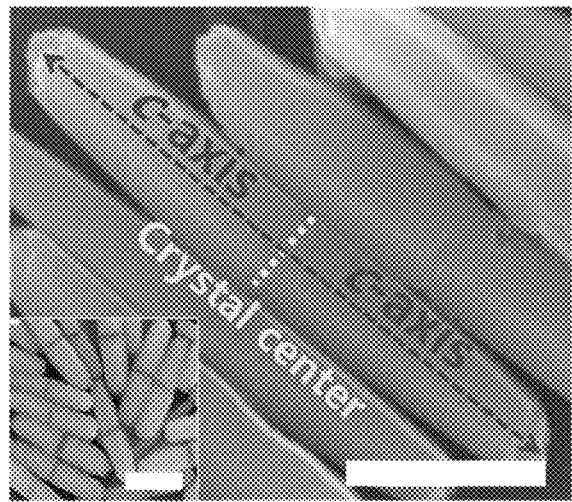
FIG. 13 is a view showing the generation of piezoelectric potential and simulation results of biaxially grown ZnO nanorods under bending stress.
Figure 13B:
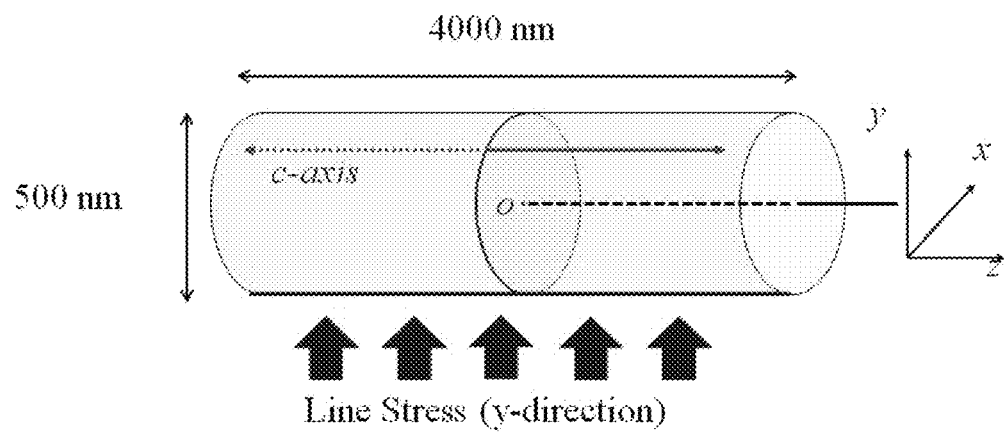
Figure 13C:
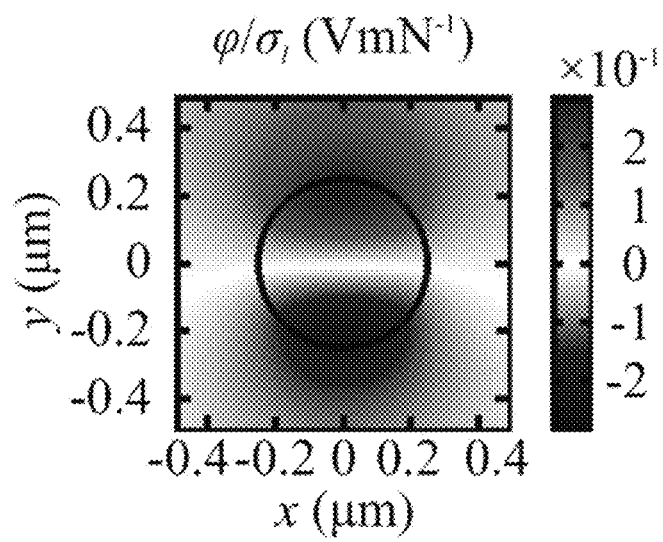
Figure 13D:
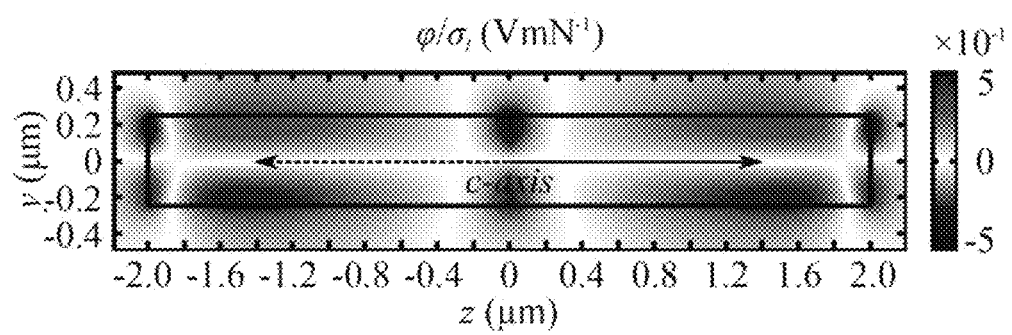

The inventors theoretically examined how biaxially-grown ZnO nanorods convert applied mechanical energy into electrical energy. FIG. 13a is an SEM image of biaxially-grown ZnO nanorods that were grown for 30 minutes at 85° C. by hydrothermal synthesis. Arrows and a dotted line indicate the direction of growth (c-axis) and the center of crystal (scale bar=1 μm). The inserted image shows biaxially-grown ZnO nanorods that were grown for 5 minutes at 85° C., and the crystal center is clearly shown (scale bar=500 nm). In the bent matrix, each of embedded biaxially-grown ZnO nanorods aligned along the in-plane direction is symmetrically bent toward the middle portion of the nanorod, and thus the symmetric bending can be considered in theoretical calculations. FIG. 13b is a schematic view showing biaxially-grown ZnO nanorods, in which Cartesian coordinates are shown (O indicates the center of a vertical plane that bisects a cylinder.). As shown in FIG. 13b, biaxially-grown ZnO nanorods can be assumed to be cylinders each having the following parameters: (1) The diameter and length of the cylinder are respectively 500 nm and 4000 nm (the cylinder is referred to as the sub-micron rod for the sake of convenience), (2) the c-axis parallel to the center-axis (which is parallel to the z-axis) of the cylinder is mirror-symmetrically aligned by the xy-plane that halves the cylinder, (3) mechanical stress and piezoelectricity linearly increase in response to external strain, (4) the elastic modulus, piezoelectric coefficient, and relative permittivity of ZnO are known (e.g. can be taken from known literatures), (5) the sign of the piezoelectric coefficient is plus (or minus) for the ZnO domain where the orientation of c-axis is in the positive or negative z-direction, and (6) the cylinder is surrounded by a dielectric material having a relative permittivity of 2.3, which is considered to be PDMS.

of FIGS. 13c and 13d show the calculated distribution of piezoelectric potential in the biaxially-grown ZnO cylinder when a mechanical load of the y-direction is applied to the line boundary of the cylinder at y=−250 nm and x=0 nm. In FIG. 13c, the piezoelectric potential (φ) corresponding to the biaxially-grown ZnO cylinder under the external line stress ($\sigma_1$) which is indicated with blue arrows. In FIG. 13d, black arrows and solid lines indicate the direction of the c-axis and the ZnO cylinder boundaries, respectively. The calculation was conducted using a finite element method. A majority of the region at the upper half (y>0) exhibits positively polarized piezoelectric potentials, whereas negatively polarized piezoelectric potentials are displayed in the lower half. This distribution of polarization is reversed near the xy-plane that bisects the cylinder. However, the net piezoelectric potential of the upper (or lower) half of the cylinder is a meaningful positive (or negative) value. That is, the piezoelectric potential is laterally symmetrical about the center of the cylinder, and thus potential is generated in the vertical direction.

Figure 13E:
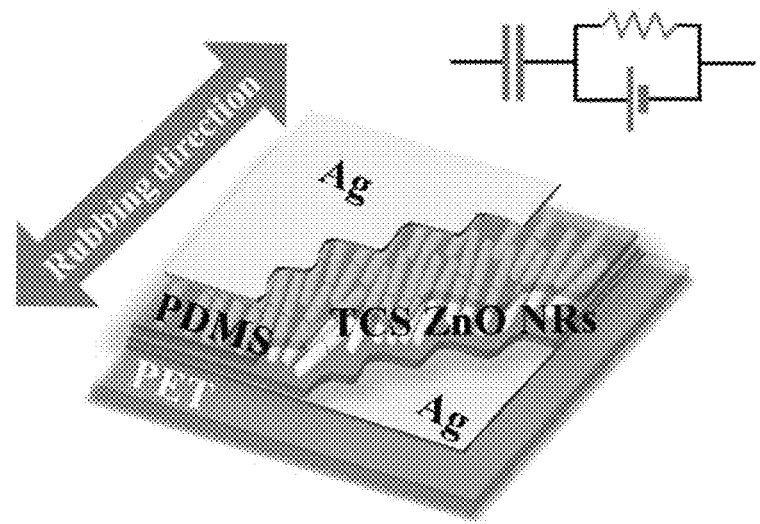

In order to experimentally verify the calculated results, a simple piezoelectric energy-harvesting devices was fabricated. A schematic circuit diagram of the piezoelectric energy-harvesting device is shown in of FIG. 13e. A single layer of SPAS of which the top and the bottom were coated with silver (Ag) electrodes was placed on a polyethylene terephthalate (PET) substrate. All such devices were operated with a 1 mm radius of bending at 0.05 Hz.

Figure 13F:
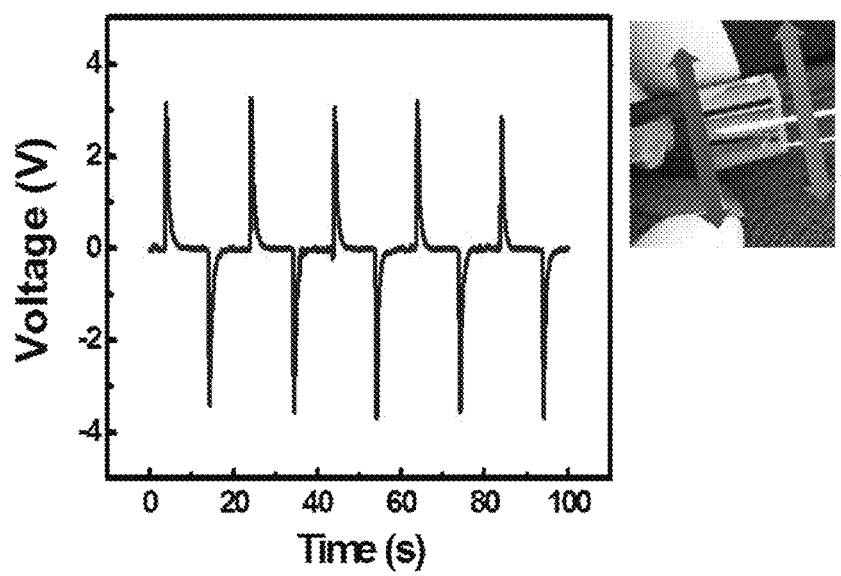
Figure 13G:
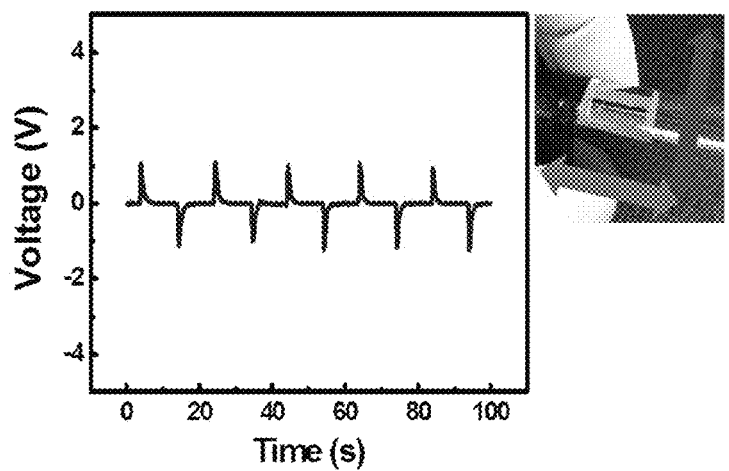
Figure 13H:
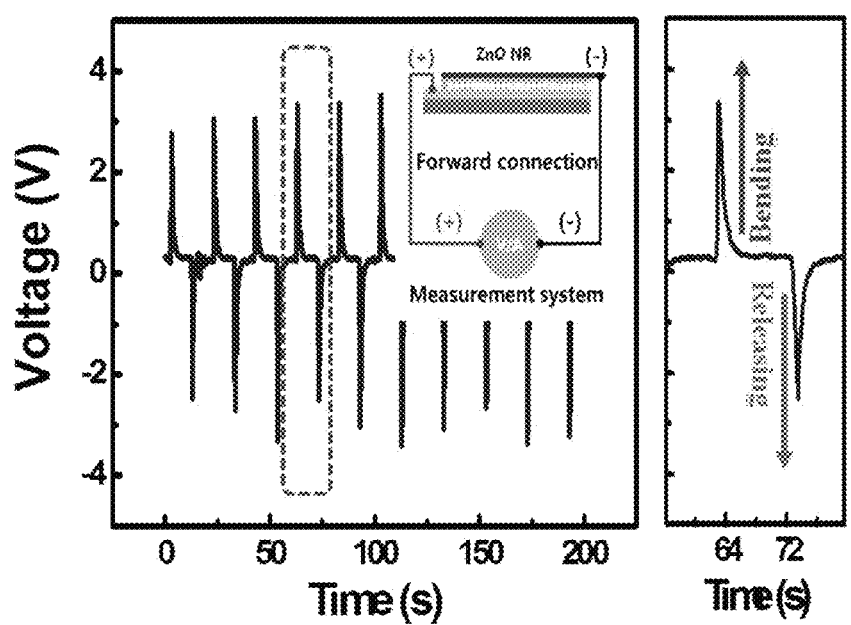
Figure 13I:
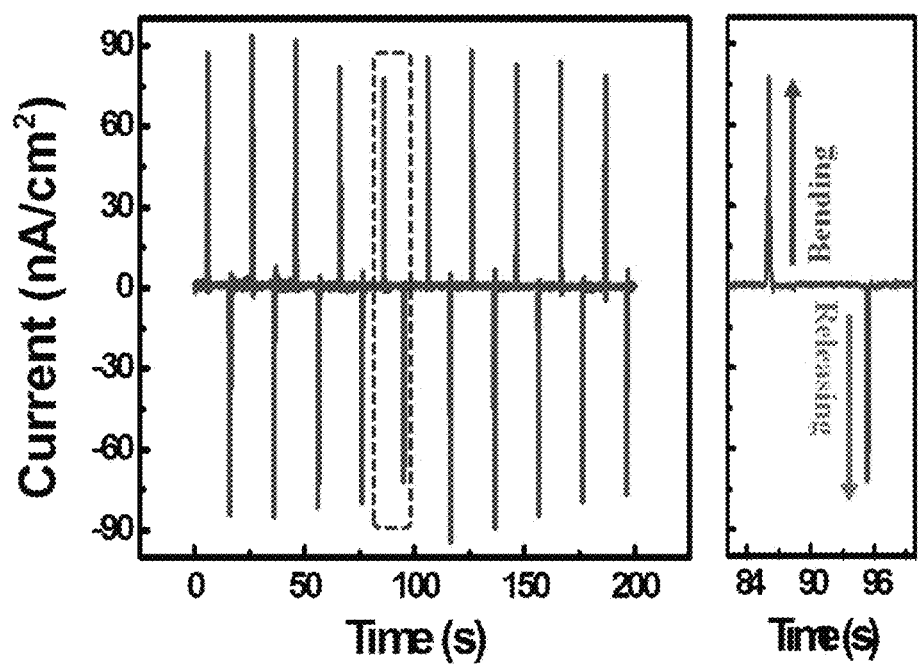

When the bending direction was changed, different voltage outputs were obtained, as shown in FIGS. 13f and 13g. As shown FIG. 13f, biaxially-grown ZnO nanorods piezoelectrically activated when they were aligned parallel in the bending direction. The voltage of the parallel bending was at least three times that of the perpendicular bending, as shown of FIG. 13g. Ideally, a voltage is not always produced through the perpendicular bending, but an output of about 1 V was measured. This voltage is thought to arise from the imperfect alignment of biaxially-grown ZnO nanorods in a particular direction. Therefore, in some cases, it is preferable that nanorods be designed to align according to specific applications.

Figure 13J:
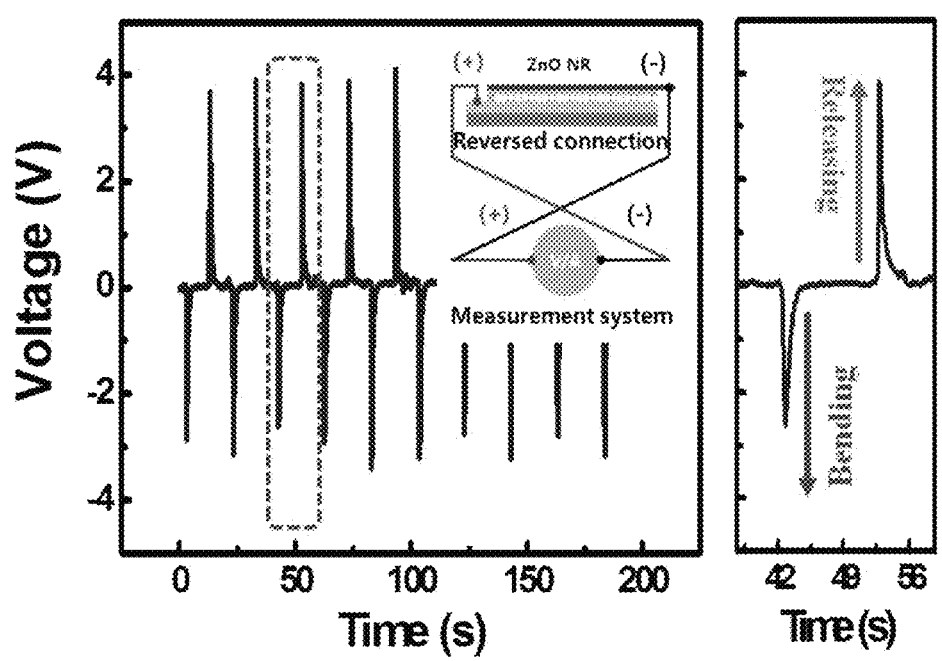
Figure 13K:
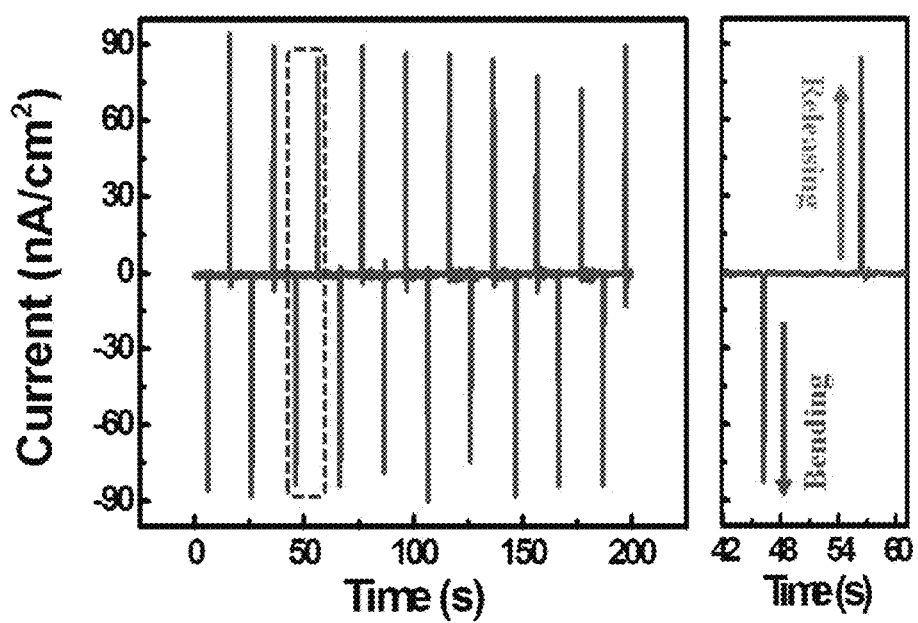

In addition, the polarity of piezoelectric potential generated by the SPAS was determined by a reverse connecting method, as shown in FIGS. 13h to 13k. As the device was bent convexly, a positive voltage and current was initially measured at the top electrode, as shown in of FIGS. 13h and 13i. This result coincides perfectly with the calculated prediction. When the direction of the electrical connection was reversed, the polarity of a voltage and current at the top electrode was measured to be negative, as shown in FIGS. 13j and 13k. Therefore, it is possible to prove that an electrical energy output from the bent SPAS originates from piezoelectrically-activated biaxially-grown ZnO nanorods which were assembled into an in-plane single layer.

As set forth above, the unit patch 10 having the piezoelectric structure (including the first PDMS, the unidirectional single layer of ZnO nanorods and the second PDMS) generates piezoelectric potential using the above-described mechanism. The generated piezoelectric potential can be effectively transferred to the skin through the PDMS to stimulate the skin, thereby helping the skin regenerate.

Although the present invention has been described hereinabove with respect to the exemplary embodiments, it should be understood that the present invention is not limited to the foregoing embodiments.

For instance, although biaxially-grown nanorods according to the foregoing embodiments have been described as being fabricated by hydrothermal synthesis, the present invention is not limited thereby. Although the hydrothermal synthesis is used to synthesize a large amount of nanorods, chemical vapor deposition (CVD) is also applicable in order to form a small amount of nanorods having high crystallinity.

In addition, although the foregoing embodiment has been described as generating piezoelectric potential using nanorods, more particularly, biaxially-grown nanorods, the present invention is not limited thereto. Uniaxially-grown nanorods can also be employed. Films having a nanometer scale, nanowires, etc., can be employed as the piezoelectric material.

As set forth above, the foregoing embodiments can be made into various alterations and modifications without departing from the scope of the appended Claims, and all such alterations and modifications fall within the scope of the present invention. Therefore, the present invention shall be defined by only the claims and their equivalents.

The invention claimed is:

1. A medical patch having an electric potential generating structure which is attachable to a wound to thus regenerate injured skin tissues, the medical patch having a piezoelectric potential generating structure comprising a plurality of unit patches stacked one on another, each of the plurality of unit patches comprising a first layer, a second layer and a plurality of piezoelectric nanorods disposed between the first and second layers, wherein when the medial patch is attached to a skin for use, the piezoelectric potential generating structure converts mechanical energy originating from a movement of muscle into a piezoelectric potential, wherein the plurality of piezoelectric nanorods comprise a plurality of biaxially-grown piezoelectric nanorods, which are aligned horizontally along with in-plane direction of the first layer or the second layer, wherein the plurality of biaxially-grown piezoelectric nanorods have an average length ranging from 2.5 µm to 3 µm and an average diameter ranging from 200 nm to 250 nm, and are symmetrically bent based on middle portion of the nanorods by the muscle movement of the skin to which the patch is attached, wherein when mechanical load is applied to the biaxially-grown piezoelectric nanorods by the muscle movement of the skin, a first half of each of the biaxially-grown piezoelectric nanorods exhibits positively polarized piezoelectric potentials and a second half opposed to the first half of each of the biaxially-grown piezoelectric nanorods exhibits negatively polarized piezoelectric potentials, wherein the first and second layers are flexible such that the medical patch is attachable to the skin for use.

2. The medical patch according to claim 1, wherein the plurality of piezoelectric nanorods is arrayed unidirectionally between the first and second layers.

3. The medical patch according to claim 2, wherein the plurality of piezoelectric nanorods is arrayed unidirectionally to form a single layer between the first and second layers.

4. The medical patch according to claim 3, wherein the first and second layers are made of a material that is able to transfer mechanical energy applied from an outside to the piezoelectric nanorods.

5. The medical patch according to claim 4, wherein the first and second layers are made of a material that is able to transfer piezoelectric potential generated from the plurality of piezoelectric nanorods to a surface thereof.

6. The medical patch according to claim 1, wherein the number of the unit patches which are stacked one on another varies depending on an intended level of potential.

7. The medical patch according to claim 6, wherein the intended level of potential is 1 V or higher.

8. The medical patch according to claim 1, wherein each of the plurality of unit patches shares at least one of the first and second layers with an adjacent unit patch of the plurality of unit patches.

9. A method of fabricating a medical patch having an electric potential generating structure which is attachable to a wound to thus regenerate injured skin tissues, the method comprising the following steps of:
(a) preparing powders of piezoelectric nanorods;
(b) forming a layer of piezoelectric nanorods by dispersing and rubbing the powders of piezoelectric nanorods on a first layer which is coated on a substrate;
(c) forming a second layer on the layer of piezoelectric nanorods; and
(d) forming a unit patch having a piezoelectric potential generating structure by separating the first layer and the substrate from each other,
wherein the piezoelectric nanorods comprise a plurality of biaxially-grown piezoelectric nanorods, which are aligned horizontally along with in-plane direction of the first layer or the second layer, wherein the plurality of biaxially-grown piezoelectric nanorods have an average length ranging from 2.5 µm to 3 µm and an average diameter ranging from 200 nm to 250 nm, wherein when mechanical load is applied to the biaxially-grown piezoelectric nanorods by the muscle movement of the skin, a first half of each of the biaxially-grown piezoelectric nanorods exhibits positively polarized piezoelectric potentials and a second half opposed to the first half of each of the biaxially-grown piezoelectric nanorods exhibits negatively polarized piezoelectric potentials, wherein the first and second layers are flexible such that the medical patch is attachable to the skin for use.

10. The method according to claim 9, wherein the step (b) comprises arraying the plurality of piezoelectric nanorods unidirectionally between the first and second layers.

11. The method according to claim 10, wherein the step (b) comprises arraying the plurality of piezoelectric nanorods unidirectionally to form a single layer between the first and second layers.

12. The method according to claim 11, wherein the first and second layers are made of a material that is able to transfer mechanical energy applied from an outside to the layer of piezoelectric nanorods and that is able to transfer piezoelectric potential generated from the plurality of piezoelectric nanorods to a surface thereof.

13. The method according to claim 12, wherein the first and second layers are flexible such that the patch is attachable to a skin for use.

14. The method according to claim 11, further comprising the step of stacking a plurality of the unit patches one on another.

15. The method according to claim 14, wherein the plurality of biaxially-grown piezoelectric nanorods is fabricated by hydrothermal synthesis.

16. A medical patch having an electric potential generating structure which is attachable to a wound to thus regenerate injured skin tissues, the medical patch comprising a unit patch having a piezoelectric potential generating structure, the unit patch comprising a first layer, a second layer and a piezoelectric nanomaterial disposed between the first and second layers, wherein the unit patch generates a piezoelectric potential by a muscle movement of the skin to which the patch is attached, without a separate electric potential generating system, wherein the piezoelectric nanomaterial is a plurality of biaxially-grown piezoelectric nanorods, which are aligned horizontally along with in-plane direction of the first layer or the second layer, wherein the plurality of biaxially-grown piezoelectric nanorods have an average length ranging from 2.5 µm to 3 µm and an average diameter ranging from 200 nm to 250 nm, and are symmetrically bent based on middle portion of the nanorods by the muscle movement of the skin to which the patch is attached, wherein when mechanical load is applied to the biaxially-grown piezoelectric nanorods by the muscle movement of the skin, a first half of each of the biaxially-grown piezoelectric nanorods exhibits positively polarized piezoelectric potentials and a second half opposed to the first half of each of the biaxially-grown piezoelectric nanorods exhibits negatively polarized piezoelectric potentials, wherein the first and second layers are flexible such that the medical patch is attachable to the skin for use.

17. The medical patch according to claim 16, wherein the plurality of piezoelectric nanorods is arrayed unidirectionally between the first and second layers.

18. The medical patch according to claim 17, wherein the plurality of piezoelectric nanorods is arrayed unidirectionally to form a single layer between the first and second layers.

19. The medical patch according to claim 18, wherein the first and second layers are made of a material that is able to transfer mechanical energy applied from an outside to the piezoelectric nanorods.

20. The medical patch according to claim 19, wherein the first and second layers are made of a material that is able to transfer piezoelectric potential generated from the plurality of piezoelectric nanorods to a surface thereof.

21. The medical patch according to claim 18, wherein the medical patch comprises a plurality of the unit patches stacked one on another.

\* \* \* \* \*